United States Patent
Wittmer et al.

(10) Patent No.: US 9,823,100 B2
(45) Date of Patent: Nov. 21, 2017

(54) METHOD AND APPARATUS FOR DETERMINING A STATE OF A MEASURING TRANSDUCER INTEGRATED IN A PROCESS CONTAINER

(71) Applicant: Endress + Hauser Conducta Gesellschaft für Mess- und Regeltechnik mbH + Co. KG, Gerlingen (DE)

(72) Inventors: Detlev Wittmer, Distelweg (DE); Thomas Steckenreiter, Frankfurt (DE)

(73) Assignee: Endress+Hauser Conducta GmbH+Co. KG, Gerlingen (DE)

(*) Notice: Subject to any disclaimer, the term of this patent is extended or adjusted under 35 U.S.C. 154(b) by 266 days.

(21) Appl. No.: 14/652,479

(22) PCT Filed: Nov. 25, 2013

(86) PCT No.: PCT/EP2013/074616
§ 371 (c)(1),
(2) Date: Jun. 16, 2015

(87) PCT Pub. No.: WO2014/095245
PCT Pub. Date: Jun. 26, 2014

(65) Prior Publication Data
US 2015/0316397 A1    Nov. 5, 2015

(30) Foreign Application Priority Data
Dec. 20, 2012 (DE) .................. 10 2012 112 782

(51) Int. Cl.
*G01N 1/00* (2006.01)
*G01D 18/00* (2006.01)
*G01N 27/416* (2006.01)

(52) U.S. Cl.
CPC .......... *G01D 18/00* (2013.01); *G01N 27/4165* (2013.01)

(58) Field of Classification Search
CPC .... G01D 18/00; G01N 27/4165; G01N 33/20; G01N 27/416
See application file for complete search history.

(56) References Cited

U.S. PATENT DOCUMENTS

| | | | |
|---|---|---|---|
| 4,527,420 A * | 7/1985 | Foote | G01N 15/02 73/61.75 |
| 5,548,597 A | 8/1996 | Kayama | |

(Continued)

FOREIGN PATENT DOCUMENTS

| | | |
|---|---|---|
| CN | 1637412 A | 7/2005 |
| CN | 101432597 A | 5/2009 |

(Continued)

OTHER PUBLICATIONS

German Search Report, German Patent Office, Munich, DE, dated Oct. 23, 2013.

(Continued)

*Primary Examiner* — Francis Gray
(74) *Attorney, Agent, or Firm* — Christopher R. Powers; PatServe

(57) ABSTRACT

A method for determining a state of a measuring transducer integrated in a process container, wherein in the process container one or more processes are being performed, and the measuring transducer registers at least one physical or chemical process parameter within the process container, includes steps as follows: identifying a process currently being performed in the process container; and ascertaining a deviation value as measure of a deviation of a measured value progression registered by the measuring transducer during the process currently being performed in the process container from a measured value progression expected for (Continued)

the identified process, wherein the state of the measuring transducer and/or of the process is determined utilizing the ascertained deviation value.

16 Claims, 3 Drawing Sheets

(56) References Cited

U.S. PATENT DOCUMENTS

| | | | |
|---|---|---|---|
| 7,290,434 B2 | 11/2007 | Ammann | |
| 2005/0166660 A1* | 8/2005 | Ammann | G01N 27/4165 73/1.01 |
| 2008/0033898 A1* | 2/2008 | Hashimoto | G01D 18/00 706/20 |
| 2013/0213807 A1* | 8/2013 | Hanko | G01N 27/4167 204/407 |
| 2015/0330934 A1* | 11/2015 | Mashevskiy | G01N 27/4168 205/786.5 |

FOREIGN PATENT DOCUMENTS

| | | | |
|---|---|---|---|
| CN | 102103113 A | 6/2011 | |
| DE | 4436658 A1 | 4/1995 | |
| DE | 10141408 A1 | 3/2003 | |
| DE | 102005003970 A1 | 8/2006 | |
| DE | 102008045840 A1 | 3/2010 | |
| EP | 1550861 B1 | 7/2005 | |
| EP | 1581880 A4 * | 2/2013 | G05B 23/0281 |

OTHER PUBLICATIONS

International Search Report, EPO, The Netherlands, dated Jan. 16, 2014.
English Translation of the International Preliminary Report on Patentability, WIPO, Geneva, CH, dated Jul. 2, 2015.
Markus Grube "Ein nues Konzept zur Diagnose electrochemischer Sensoen am Beispiel von pH-Glaselektroden", Feb. 4, 2011.

* cited by examiner

METHOD AND APPARATUS FOR DETERMINING A STATE OF A MEASURING TRANSDUCER INTEGRATED IN A PROCESS CONTAINER

TECHNICAL FIELD

The invention relates to a method for determining a state of a measuring transducer integrated in a process container and to an apparatus for performing the method.

BACKGROUND DISCUSSION

Applied In process measurements technology and in the field of gas- and liquid analysis are measuring systems for registering physical and/or chemical to measured variables. Measuring transducers are components of such measuring systems. Important measured variables in process measurements technology and in gas-, respectively liquid, analysis are temperature, pressure, flow and fill level, as well as especially analytical parameters of measured media, e.g. their pH-value, conductivity, concentrations of certain ions or other chemical substances, such as, for example, oxygen, carbon dioxide, organic substances or nutrients in the measured media. These analytical parameters play a role in various applications, for example, in laboratory or in process, respectively analytical measurements, technology in the fields of chemistry, pharmacy, biotechnology, food technology or environmental technology.

Fundamentally, a measuring transducer transduces the registered measured variable into an electrical signal, which is correlated with the measured variable via a characteristic curve for the measuring transducer. The measurement signal present firstly as an electrical signal, for example, a measurement voltage, can be further processed by means of an evaluation circuit and output in the units of the measured variable to be ascertained and displayed.

Measuring systems used in process measurements technology or in analytical measurements technology can comprise a housing, in which are integrated the measuring transducer, the evaluation circuit and a display device. For more complex evaluations, especially for storing and/or processing measured values and/or for control of processes using the measured values registered by the measuring system, the measuring system can include means for data processing. This can be embodied, for example, as a data processing system in the form of a measurement transmitter, a computer or a programmable logic controller. Applied in analytical measurements technology in many applications are measuring transducers, whose lifetime is significantly shorter than that of the display apparatus or the means for data processing. This is true, for example, in the case of measuring transducers such as pH-sensors, ion-selective electrodes, optical or amperometric sensors for registering concentrations of certain substances in the measured medium. Frequently in these applications, the measuring transducers are embodied as exchangeable units, e.g. in the form of measuring probes, which are separate from the display device or the means for more extensive data processing, and communicate with these via a cable connection or wirelessly. In such case, at least a part of the evaluation circuit, for example, the on-site electronics, can be a component of the exchangeable measuring transducer unit.

Real measuring transducers deviate with time ever more strongly from ideal behavior due to aging from the influence of external conditions loading the measuring transducer, as well as also due to inner changes. This deviation from ideal behavior results in a shifting of the measuring transducer characteristic curve. It is, consequently, established practice to service the measuring transducer from time to time and, in given cases, to perform a compensation of the deviation. This is quite usual in the case of electrochemical measuring transducers, such as pH-electrodes, ion-selective electrodes, amperometric oxygen sensors, especially dissolved oxygen sensors, as well as other amperometric measuring transducers and also in the case of conductivity sensors. Such a compensation, in the case of which the display value of the measuring transducer is adjusted to the true value of the measured variable, is referred to as adjustment. Since in process measurements technology, however, the not quite fitting terminology "calibration" is, as a rule, used for this procedure, this terminology will be maintained here and in the following.

The end of the lifetime of the measuring transducer is reached when its aging has progressed so far that, in spite of calibration, reliability of the measured values delivered by the measuring transducer is no longer assured. In this case, depending on type of measuring system, either the entire measuring system is taken out of operation and replaced by a new one, or the measuring transducer is replaced.

The aging of a measuring transducer, which leads to a change of the transfer function, depends also on environmental conditions, to which the measuring transducer is exposed. Thus, it is known, for example, that high temperatures accelerate shift the aging process. Also, measuring transducers, which during operation come in contact with chemically aggressive, measured media, for example, strong acids or alkaline solutions, or which are exposed to strong mechanical loadings, e.g. measuring transducers, which are exposed during operation to a medium with high entrained dirt loads or high pressures, can disproportionately rapidly age.

Described in German patent, DE 101 41 408 A1 is a method for determining the calibration interval time, i.e. amount of time between two calibrations, of electrochemical measuring transducers. The method explained in greater detail using the example of a pH-sensor includes sequential registering during the operation of the measuring transducer of at least one measurement parameter relevant for judging the aging of the sensor. Examples of such relevant measurement parameters include temperature and pH-value. A predetermined base calibration interval time, which is fixed under the proviso that the monitored measurement parameters lie in a basic value range only little influencing the aging of the sensor, can be adapted based on the registered measurement parameter in an ongoing manner when extreme values of the measurement parameter occur, which lead to an accelerated aging of the measuring transducer.

This method takes into consideration, indeed, the influence of extreme values of the monitored measurement parameter on the aging of the measuring transducer, however, it neglects the disproportionate influence of especially demanding processes, since it is not designed to identify such processes and correspondingly to take them into consideration.

Described in European patent, EP 1 550 861 B1 is a method for determining the state of a measuring transducer, which is integrated in a containment, and which is cleaned from time to time without being deinstalled, for example, using known CIP- (cleaning in place) or SIP- (sterilization in place) methods. The method includes monitoring the temperature as a function of time, wherein based on the temperature as a function of time, especially in comparison with threshold values, it is detected that a CIP- or SIP method has taken place. The loading of the measuring transducer associated with the established method is registered, the sum all loadings ascertained and by comparison with a maximum value of the allowable loadings, an allowable remaining loading or remaining life is calculated.

This method enables consequently the identification of CIP- or SIP-processes, to which the measuring transducer is exposed, and taking such into is consideration in determining the state of the measuring transducer.

Disadvantageous, however, is that the state of the measuring transducer is determined based on temperature, respectively the process acting on the measuring transducer, based on the load resulting therefrom for the measuring transducer. The determining of sensor state based on the loadings experienced by the sensor can, however, only be a coarse estimation, which neglects that the aging of various examples of the same sensor type is influenced in different degrees by one and the same loading, due to manufacturing related variations. Since the method described by EP 1 550 861 B1 does not take such sample variations into consideration, considerable error can occur in determining the state of the measuring transducer.

SUMMARY OF INVENTION

It is, consequently, an object of the invention to provide a method overcoming the disadvantages of the known methods for determining the state of a measuring transducer integrated in a process container.

This object is achieved by a method for determining a state of a measuring transducer integrated in a process container, wherein in the process container one or more processes are being performed, and the measuring transducer registers at least one physical or chemical process parameter within the process container, includes steps as follows:

identifying a process currently being performed in the process container,
ascertaining a deviation value as measure of a deviation of a measured value progression registered by the measuring transducer during the process currently performed in the process container from a measured value progression expected for the identified process, wherein the state of the measuring transducer and/or of the process is determined utilizing the deviation value.

The process container can, depending on type of process monitored by the is measuring transducer, be, for example, a media conveying, liquid transport line, a reactor or a fermenter. The measuring transducer can be connected with the process container by means of a process connection.

In order that the process currently being performed in the process container can be identified, a corresponding load acting on the measuring transducer due to the action of the process can be derived. This loading can enter into determining the state of the measuring transducer. The deviation value, which is a measure of a deviation of the measured value progression registered by the measuring transducer during the process currently performed in the process container, thus of the currently registered, measured value progression, from the measured value progression expected for the identified process, reflects, moreover, the actual state of the measuring transducer: the more strongly the measured value progression actually registered by the measuring transducer and output deviates from the expected measured value progression of the identified process, the more strongly the measuring transducer also deviates from its ideal behavior. By taking the deviation value into consideration in determining the state of the measuring transducer, consequently, besides the nominal loading of the measuring transducer due to the current process also the current actual state of the measuring transducer is taken into consideration.

The process currently performed in the process container can be identified, for example, based on the measured value progression of the process parameter currently registered by means of the measuring transducer.

In an embodiment, the process currently performed in the process container can be identified based on at least one measured value progression of the process parameter currently registered by means of the measuring transducer. If the measuring transducer is, for example, embodied to register measured values of the temperature, then the process can be identified based on the registered progression of the measured values of temperature. If the measuring transducer registers supplementally or alternatively, for example, the pH-value, a concentration, a conductivity or a pressure, then the process can be identified based on the registered progression of this parameter. As will be explained in greater detail below, also other measured variables, which are registered by means of one or more auxiliary measuring transducers, can be taken into consideration for identification of the process currently performed in the process container.

For an identification based on the registered measured value progression, not only an identification based on the total progression of the measured value as a function of time is meant here and in the following. Rather, also an identification based on characteristic features of the measured value progression is included. Characteristic features of a measured value progression can include, for example, a global or local maximum value, a global or local minimum value, a slope, a superimposed noise, a spectrum, a plateau, a gradient, an exceeding of a threshold value or a subceeding of a threshold value.

For identification of the process based on the currently registered, measured value progression, the currently registered, measured value progression, respectively its characteristic features, can be compared with at least one expected measured value progression, which represents a predetermined process class, and, in the case of sufficiently small deviation of the currently registered, measured value progression from the expected measured value progression, the process currently performed in the process container and providing the basis for the currently registered, measured value progression, can be identified as a process of the predetermined process class.

A process class can be, for example, a sterilization method for sterilizing the process container with the therein integrated measuring transducer, thus a so-called SIP method (SIP=sterilization in place). Also other process classes can be predetermined, for example, one or more different cleaning methods, in the case of which the process container with the therein integrated measuring transducer is flowed through by a cleaning liquid, in given cases, at elevated temperature. Such methods are also referred to as CIP methods (CIP=cleaning in place). Moreover, also a method performed in the process container for manufacture or processing of a chemical or food product can form a process class. Each process class has at least one expected measured value is progression of at least one process parameter, e.g. temperature, pH-value, pressure, conductivity.

The currently registered, measured value progression and the expected measured value progression can be compared based on one or more features of the measured value progressions, especially based on the measured value progression, a gradient of the measured value progression, an exceeding of a threshold value, a subceeding of a threshold value, a local or absolute extreme of the measured value progression, a noise superimposed on the measured value progression or a plateau of the measured value progression.

The process currently performed in the process container can in an embodiment of the method of the invention be identified by means of a classifier, in that the classifier associates the currently registered, measured value progression or at least one or more features of the measured value progression with a predetermined process class and determines as deviation value a probability, with which the current measured value progression represents a process of the process class.

A classifier is a method for classification, which can also be embodied in the form of a computer program product. Such a machine classifier includes a learning algorithm, which building on a known database of expected measured value progressions learns one or more expected features of one or more process classes, e.g. SIP method, CIP method, production process- or treatment method, as well as an evaluating algorithm, which associates a new and previously not-identified process with one of these process classes due to a comparison of its features with the learned features. A machine classifier can be, for example, a neural network, a polynomial classifier or a fuzzy classifier. The classifier can especially be embodied in such a manner that it ascertains a probability, with which the process currently performed in the process container is a process of the associated process class. This probability or a therefrom derived value can serve in the present method as a deviation value. The process can be associated with that process class, for which the ascertained probability is the highest.

In the learning phase, the classifier can access, for example, one or more expected measured value progressions of the at least one process parameter, wherein each measured value progression represents a process class. If, for example, alternately, an SIP method, a CIP method and a method for synthesis of a chemical compound are performed in the process container, then the classifier can access in the learning phase expected progressions of the measured value progressions registered by the measuring transducer at its location of installation together with information concerning to which of these methods the measured value progressions respectively belong. The classifier learns in the learning phase, based on this database, expected features of a measured value progression of the process class "SIP method", corresponding expected features of the process class "CIP method", and corresponding expected features of the process class "synthesis methods", in that it extracts these features from the corresponding process progressions and associates them with the respective process classes.

After termination of the learning phase, the classifier can compare the measured values registered by the measuring transducer, in an ongoing manner, with the learned expected features of the different process classes and, in each case, determine an agreement in the form of deviation values associated with the process classes. To the extent that, in such case, for a process class a sufficiently low deviation from the learned expected features and therewith a high probability results, that the process belongs to a process class, the process is identified as a process belonging to this process class.

The one or more expected measured value progressions can be predetermined based on pretrials using at least one measuring transducer different from the to measuring transducer, but comparable as regards accuracy of measurement, dynamic range and measuring range of the measuring transducer integrated in the process container at the location of use.

In another embodiment, the process currently performed in the process is container can be identified based on information concerning process control of the process currently performed in the process container. For example, the process control can for performing the method provide to the evaluation circuit of the measuring transducer information concerning processes currently initiated or monitored by the control unit.

In an additional embodiment, the process currently performed in the process container can be identified based on information input by a user of a measuring- and evaluation circuit of the measuring transducer.

The deviation value can in both above set forth embodiments be ascertained by a comparison of the measured value progression expected for the identified process with the currently registered, measured value progression. Especially, an option is to ascertain the deviation value based on a comparison of one or more features of the expected measured value progression with one or more corresponding features of the currently registered, measured value progression. The features can include, such as above already mentioned, for example, exceedings of threshold values, local or global extrema, noise, a spectral composition of the measurement signal, a plateau of the measured value progression, etc.

The one or more processes can be performed repeatedly in the process container during the lifetime of the measuring transducer, a change of the respectively ascertained deviation values determined, and the state of the measuring transducer determined based on the change. If, for example, an (abrupt) change of the deviation values is ascertained, respectively the change exceeds a predetermined threshold value, then it can be deduced therefrom that the actual state of the measuring transducer has (abruptly) changed. This can serve as indication of an impending failure of the measuring transducer. Especially, an alarm threshold value for the change of the deviation values can to be predetermined. If this threshold value is exceeded, then an alarm can be triggered, which indicates an immediate need for maintenance of the measuring transducer and/or for immediate replacement of the measuring transducer.

For determining the state of the measuring transducer, for example, a time development of the repeatedly ascertained deviation values can be used for determining the state of the measuring transducer, especially for predicting a remaining life of the measuring transducer. With increasing length of use of the measuring transducer, which is accompanied by an increasing total loading of the measuring transducer by the processes, to which it is exposed, also an increasing deviation of the measuring transducer behavior from the expected behavior is to be expected. This results in a deviation value trend toward increased deviations between the currently registered, measured value progression and the expected measured value progression. Correspondingly, a time development can be taken into consideration for trend determination of the sensor state and therewith especially also for determining a remaining life or a time to next calibrating.

By means of a predetermined quality criterion, the currently ascertained deviation value can either be classified as tolerable or as not tolerable, and in the case, in which the deviation value is classified as not tolerable, a warning or an alarm triggered.

By means of the measuring transducer itself or by means of an additional, auxiliary, measuring transducer likewise integrated in the process container, at least one supplemental parameter can be registered, which enters into determining the state of the measuring transducer and, in given cases, into an additional determining of a state of the process currently being performed in the process container. The registered supplemental parameter can especially serve to distinguish between a deviation of the measuring transducer from the expected behavior and a deviation of the process from the expected behavior. The supplemental parameter can be, for example, a supplemental process parameter. Equally, the supplemental parameter can be an auxiliary variable dependent on the actual state of the measuring transducer (for example, in the case of a pH-sensor, a membrane resistance or a diaphragm resistance).

Since the supplemental parameter can be one or more other process parameters, e.g. pressure, temperature, pH-value, flow, the concentration of a substance in a medium present in the process container or one or more other supplemental parameters and taken into consideration in the state determination, it can be distinguished whether an ascertained deviation of the currently registered, measured value progression from an expected measured value progression is caused by a deviation of the measuring transducer from the expected behavior or a deviation of the process from an expected behavior.

Preferably, the mentioned classifier is embodied to evaluate, based on the one or more supplemental parameters supplemental to the measured value progression registered by the measuring transducer, whether the cause for a detected deviation of the measured value progression from an expected measured value progression is caused by a defect or a maintenance need of the measuring transducer and/or whether the process performed in the process container is not running as desired.

The classifier can classify the state and/or the process in one of four predetermined classes, "measuring transducer and process in order", "process in order, measuring transducer malfunctioning", "measuring transducer in order, process malfunctioning" and "measuring transducer malfunctioning, process malfunctioning".

The measuring transducer can in a preferred embodiment register measured value progressions of at least two different process parameters, wherein the process currently performed in the process container is identified, for example, based on the currently registered, measured value progressions, and wherein, relative to a process parameter, preferably relative to all process parameters, in each case, a deviation value is ascertained as a measure of a deviation of a measured value progression registered by the measuring transducer during the process currently performed in the process container from a measured value progression expected for the identified process.

The ascertaining of the deviation value and the determining of the state of the measuring transducer based on the ascertained deviation value can be performed by an evaluation circuit, which is at least partially a component of the measuring transducer and/or at least partially a component of a superordinated is data processing unit connected with the measuring transducer, especially a measurement transmitter, a computer or a programmable logic controller.

The invention relates to also an apparatus for performing the method according to one of the above described embodiments, comprising: a process container and at least one measuring transducer integrated therein; an evaluation circuit comprising at least one processor and a program memory for performing a program furnished in the program memory for identifying a process currently performed in the process container, for ascertaining a deviation value as measure for deviation of a measured value progression registered by the measuring transducer during the process currently being performed in the process container from a measured value progression expected for the identified process, and for ascertaining the state of the measuring transducer and/or of the process utilizing the deviation value.

BRIEF DESCRIPTION OF THE DRAWINGS

The invention will now be explained in greater detail based on examples of embodiments illustrated in the appended drawing, the figures of which show as follows.

DETAILED DISCUSSION IN CONJUNCTION WITH THE DRAWINGS

Figure 1:
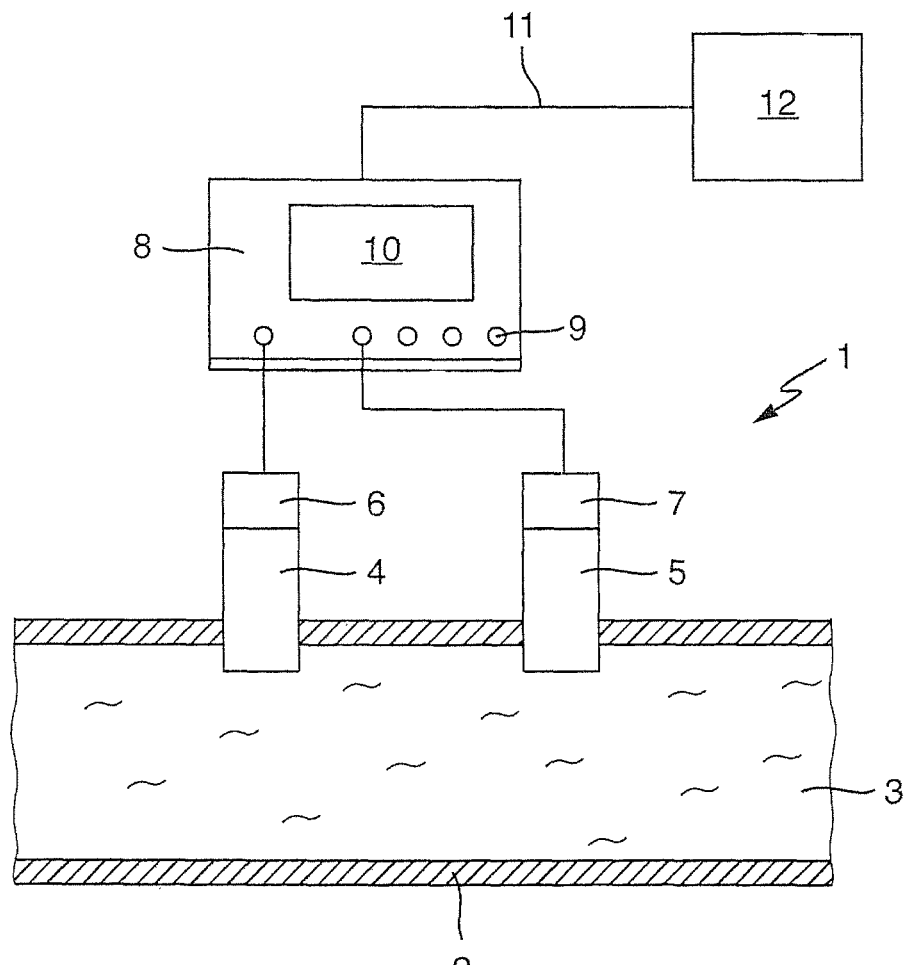
FIG. 1 is a measuring arrangement including a process container and therein integrated measuring transducers.

FIG. 1 shows schematically a measuring arrangement 1 for registering and monitoring process parameters of an industrial process. Integrated in a process container 2, which in the present example is formed by a media conveying pipe, are two measuring transducers 4 and 5, each of which registers a measured variable of a process medium 3 flowing through the process container 2. In the present example, each of the measuring transducers 4, 5 is a pH-sensor with supplementally integrated temperature measuring transducer. It is, however, also possible that the two measuring transducer are embodied, to register different measured variables, e.g. one measuring transducer could be a pH-sensor with integrated temperature sensor and the second measuring transducer could be a conductivity sensor. Basically, the measuring arrangement can supplementally or alternatively have measuring transducers for registering pressure, temperature or for determining substance concentrations in the process medium 3. Of course, also more than two measuring transducers can be integrated in the process container 2. The measuring transducers 4 and 5 have housings, in which measurement circuits are integrated. The measuring circuits comprise, in each case, means for producing a digitized, measured value signal and are embodied to output the signal to a superordinated unit, here a measurement transmitter 8. Measurement transmitter 8 includes a data processing means, which is embodied to subject signals obtained from the measuring transducers 4, 5 to additional evaluation. The data processing means of the measurement transmitter 8 and the measuring circuits of the measuring transducers 4, 5 form in the present example together an evaluation circuit, which serves for registering and processing, especially evaluation, of measured values registered and recorded by the measuring transducers 4, 5. The evaluation circuit can in an alternative embodiment also be embodied completely in the measuring transducer, completely in the measurement transmitter or distributed among a number of other units.

The superordinated unit, here the measurement transmitter 8, can exchange energy and data with individual or all measuring transducers 4, 5 via a cable connection. Individual or all measuring transducers can alternatively or supplementally communicate with the superordinated unit via a radio connection. Measurement transmitter 8 includes input means 9, e.g. keys or rotate-press switches, and a display element 10, e.g. a display. Input means and display element can also be integrated in a single unit, e.g. in the form a touch-screen. By means of the input means 9 and of the display element 10, a user can cause output of measured values as well as bring about other evaluations of the signals provided by the measuring transducers 4, 5 and represent such by means of the display element 10. Measurement transmitter 8 is connected via a communication connection, for example, a fieldbus, with a process control station 12.

The process container 2 can be a component of a process installation, which serves, for example, for manufacturing a chemical, pharmaceutical or food product. In operation of the process installation, there are performed in the process container 2, as a rule, sequentially, especially cyclically, different processes, namely at least one production process, which serves for manufacturing the corresponding product, as well as regularly performed cleaning- or sterilization processes.

Figure 2:
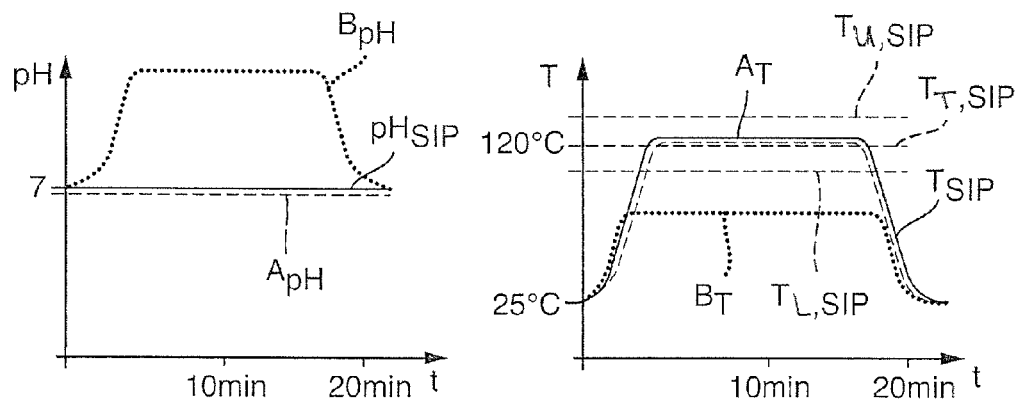
FIG. 2 is an expected measured value progression of the process parameters, temperature and pH-value, in the case of performing an SIP-process in the process container of FIG. 1.

FIG. 2 shows the typical progression of the pH-value $pH_{SIP}$ and temperature $T_{SIP}$ in the case of an SIP-process (=sterilization in place), i.e. a sterilization process, in the case of which the process container 2 with the measuring transducers 4, 5 integrated therein is sterilized by leading superheated steam through the process container 2 (solid lines). The superheated steam in the case of SIP-processes should have in general a temperature of at least 120° C. The parts to be sterilized, i.e. here the process container 2 and the measuring transducers 4, 5, should, in such case, be exposed to the superheated steam for a time of at least 20 to 30 minutes. The pH-value remains during the SIP method essentially constant within the neutral region. The progressions of the pH-value and the temperature illustrated in FIG. 2 as solid lines represent, thus, the expected measured value progressions $pH_{SIP}$, $T_{SIP}$ of the two process parameters pH-value and temperature during an SIP-process.

Figure 3:
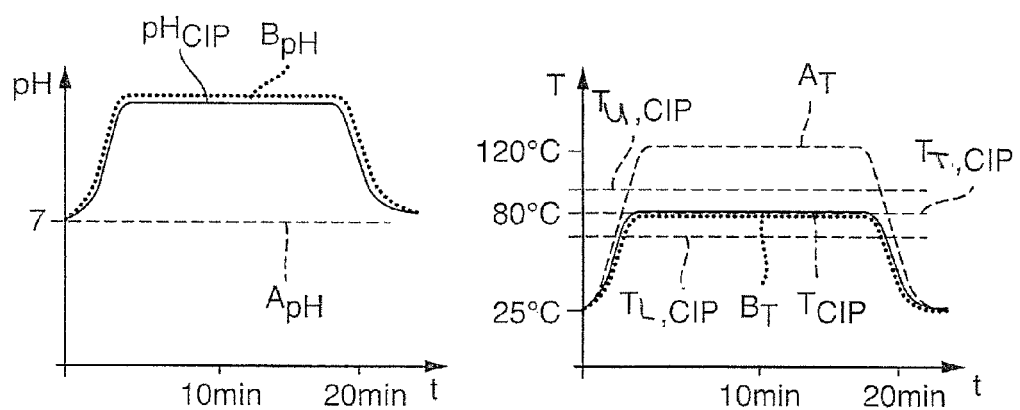
FIG. 3 is an expected measured value progression of the process parameters, temperature and pH-value, in the case of performing a CIP-process in the process container of FIG. 1.

FIG. 3 shows a typical progression of the pH-value $pH_{CIP}$ and temperature $T_{CIP}$ in the case of a CIP process (=cleaning in place), i.e. a cleaning process, in the case of which the process container 2 with the measuring transducers 4, 5 integrated therein is cleaned (solid lines). In the example illustrated here, the CIP-process includes a rinsing of the process container with the measuring transducers 4, 5 integrated therein with hot sodium hydroxide for a time of at least 20 minutes, followed by a rinsing with deionized water. Correspondingly, the progression of the pH-value shows a rise to over pH 13 during the period of time of the rinsing with sodium hydroxide. During the subsequent rinsing with deionized water, the pH-value falls to a value of pH 6. The temperature $T_{CIP}$ rises during the rinsing with hot sodium hydroxide to over 80° C. and then falls as a result of the following rinsing with deionized water. The measured value progressions $P_{CIP}$, $T_{CIP}$ illustrated in FIG. 3 as solid lines correspond thus to the expected measured value progressions of the parameters pH-value and temperature during a CIP-process.

In the following now some examples of identifying a process performed in the process container 2 based on a measured value progression registered by at least one of the measuring transducers 4, 5 will be described. Although in these Examples only measured values of pH-value and temperature are considered, of course, in equal manner, also measured values of other process parameters, such as conductivity, substance concentrations or pressure, can be taken into consideration. Although the invention is described here using the examples of cleaning- or sterilization processes, it can equally be applied to other processes, for example, production- or working processes.

The identifying of a CIP- or SIP-process can occur, for example, by associating with a predetermined process class the measured value progression currently registered by at least one of the measuring transducers 4, 5 for the process currently being performed in the process container. In the present case, three process classes are predetermined, namely the process class "SIP-process", the process class "CIP-process" and the process class "other process". The terminology, other process, means here any process, which is neither an SIP-process nor a CIP-process.

FIRST EXAMPLE

In a first example, features representing expected measured value progressions of the SIP- and CIP-processes are furnished in a memory of the measurement transmitter 8. These features are referred to in the following also as "expected features". In the present case, a first expected feature of the temperature as a function of time during an SIP-process is the exceeding of a threshold value of 120° C. A second expected feature of the temperature as a function of time is a plateau of the temperature as a function of time following the exceeding of the threshold value and remaining at over 120° C. for at least 20 min.

A first expected feature of the temperature as a function of time in the case of a CIP-process is an exceeding of a threshold value of 80° C. A second expected feature of the temperature as a function of time is a plateau of the temperature as a function of time following the exceeding of the threshold value and remaining at over 80° C. for at least 20 min.

An expected feature of the pH-value progression in the case of an SIP-process is the pH-value remaining constant in the neutral region for a time of 20 min. A first expected feature of the pH-value curve in the case of a CIP-process is the exceeding of a threshold value of pH=13. A second expected feature of the pH-value progression in the case of a CIP-process is a plateau of the pH-value curve remaining at over pH=13 for at least 20 min after exceeding the threshold value.

Of course, other features for the comparison between the current and an expected measured value progression can be taken into consideration.

Based on these furnished, expected features, a process currently being performed in the process container 2 can be identified by associating it with one of the predetermined process classes "CIP-process", "SIP-process" or "other process". For this, all or only certain of the furnished expected features can be taken into consideration. In the following, for purposes of simplicity, only identification based on the measured values of temperature is described. In equal manner, however, supplementally or alternatively, also the pH-measured values can be taken into consideration.

At least one of the measuring transducers 4, 5 registers, in an ongoing manner, measured values of the temperature and outputs these to the measurement transmitter 8. This includes data processing means, which are embodied to compare the currently registered, measured value progression, in an ongoing manner, with the expected features of temperature as a function of time.

The measured value progressions of the pH-value ApH, respectively the temperature AT, shown as dashed lines in FIGS. 2 and 3 were registered by the measuring transducer 4 during the performing of a first process A in the process container 2. The measured value progression of the pH-value BpH and the temperature BT shown as dotted lines in FIGS. 2 and 3 were registered from the measuring transducer 4 during the performing of a second process B in the process container 2. For identifying the processes A and B, the measured value progressions are then checked by the measuring transducer 8 as to what extent they have the furnished features expected for a CIP- or SIP-process.

For this, there are furnished in the memory of the measurement transmitter 8 besides the expected features of the CIP- and SIP-processes supplementally tolerance ranges, for example, in the form of upper and lower threshold values. In the present case, with reference to the first expected feature of the SIP-process, that the measured value progression exceeds a threshold value $T_{T, SIP}$ of 120° C., upper and lower tolerance threshold values at $T_{U, SIP}$=135° C. and at $T_{L, SIP}$=110° C. are furnished. Based on this tolerance range, a deviation value of the current measured value progression from the expected measured value progression can be ascertained: In the present example, the temperature progression BT reaches a value of 118° C. It thus exceeds the lower tolerance threshold value $T_{L, SIP}$, however, not the expected threshold value $T_{T, SIP}$. Serving as deviation value in the present example is the relative deviation of the actual measured value with reference to the range between the expected value from 120° C. and the lower tolerance threshold value from 110° C. In the present case, the deviation value thus amounts to 0.2.

Corresponding tolerance ranges for the expected features of the CIP-process are furnished. For example, relative to the expected feature of exceeding a threshold value $T_{T, CIP}$ of 80° C. for a CIP-process, an upper tolerance threshold value $T_{U, CIP}$ of 90° C. and a lower tolerance threshold value $T_{L, CIP}$ of 70° C. can be predetermined. A comparison of the temperature AT as a function of time with the expected features of the CIP-process leads to registering of the exceeding of the temperature threshold value of 80° C., so that the first expected feature is consequently fulfilled. However, a comparison of the actually registered measured value of temperature from 118° C. with the expected temperature value $T_{T, CIP}$ of 80° C. with reference to the interval between the upper tolerance threshold value $T_{U, CIP}$ of 90° C. and the expected value of 80° C. yields a relative deviation of 3.8 as deviation value.

A corresponding comparison is also performed relative to the second expected feature, the respective plateau length of the temperature measured value progression for the CIP-process, respectively the SIP-process, and corresponding deviation values ascertained. In the present instance, the evaluation means of the measurement transmitter 8 establishes that the deviation values relative to the expected features of the SIP-process are smaller than the deviation values relative to the expected features of the CIP-process. The process A is, consequently, associated with the process class "SIP-process" and, thus, identified as an SIP-process.

Based on a comparison of the currently registered, measured value progressions ApH, BpH, and BT with the expected features and the associated tolerance threshold values, in analogous manner as was described for temperature as a function of time AT, deviation values can be ascertained and the processes A and B identified based on the deviation values. Especially, by using the measured value progression of the pH-value ApH, the identifying of the process A as an SIP-process done based on temperature as a function of time can be verified.

For determining the state of the measuring transducer as a function of the type of the identified process, a certain loading due to such process can be associated with the measuring transducer. With each SIP-process, which the measuring transducer experiences, there is a corresponding loading value associated with the SIP-process, wherein all loading values associated with the measuring transducer are summed up to a total loading. The total loading corresponds to the sum of the loading values accumulated over the lifetime of the measuring transducer. In the simplest case, recognition of the loading can occur by incrementing a loading counter by a predetermined value. Correspondingly, also with each CIP-process, which the measuring transducer experiences, a predetermined loading value can be associated with that too, wherein the loading values due to CIP-processes likewise adds to the total loading. The total loading is a possible measure for the state of the measuring transducer. If it reaches a predetermined maximum loading value, the end of the lifetime of the measuring transducer has been reached. Upon reaching or shortly before reaching the maximum loading value, the measurement transmitter 8 can output an alarm via the display element 10 or to the control station 12.

The deviation values ascertained for identifying the process being performed currently in the process container 2 can likewise be taken into consideration for ascertaining the measuring transducer state. This is explained in greater detail below.

SECOND EXAMPLE

In a second example of an embodiment, the process currently being performed in the process container 2 and the deviation value representing the deviation of the measured value progression currently registered during the process are determined by means of a classifier.

The classifier can be a computer program product stored in the measurement transmitter 8 and executable by such. The classifier includes a learning algorithm, to which in a learning phase a series of measured value progressions of later to be identified processes are presented. Based on the presented measured value progressions, the classifier learns one or more expected features and/or one or more expected measured value progressions for the different possible process classes, e.g. in the here considered example the process classes, "SIP-process", "CIP-process" and "other process". Of course, an option is that the classifier also learns expected measured value progressions, respectively expected features of other processes, especially of production- or working processes.

For example, the classifier in the learning phase can be presented with a library of measured value progressions of various processes, especially of CIP- or SIP-processes. In a preferred form of embodiment, the classifier is provided measured value progressions, which are registered during the performing of the processes, e.g. the SIP- or CIP-processes, in the process container 2 by a measuring transducer 4, 5 integrated therein. In this way, the classifier learns the expected measured value progressions at the concrete measuring point within the process container, in which the measuring transducer 4, 5 is applied, and thus takes into consideration the concrete installed situation of the measuring transducer 4, 5. This permits an essentially more exact identifying of the processes after expiration of the learning phase than when the measurement transmitter 8 is provided expected measured value progressions based only on "typical" measured value progressions in an ideal situation or only in a differing installed situation.

After termination of the learning phase, the classifier can by means of an to evaluating algorithm compare the measured value progressions ApH, AT, BpH, BT registered by the measuring transducer in an ongoing manner with the learned expected features of the different process classes and, in each case, determine a measure of the agreement, respectively deviation, in the form of deviation values associated with the process classes. To the extent that, in is such case, for a process class, a deviation value representing a sufficiently low deviation results, the process is identified as a process belonging to this process class. The classifier can especially be embodied in such a manner that it ascertains as a deviation value a probability, with which the process currently being performed in the process container is a process of the associated process class.

The machine classifier can be, for example, a neural network, a polynomial classifier or a fuzzy classifier.

In the present example, the classifier ascertains based on a comparison of the measured value progressions of pH-value and temperature of the process A with the expected measured value progressions illustrated in FIGS. 2 and 3 a smaller deviation compared with the expected measured value progression for the process class, SIP-process, than with the expected measured value progression for the process class CIP-process. The process A is, consequently, identified as an SIP-process. In contrast, the classifier ascertains based on a comparison of the measured value progressions of pH-value and temperature of the process B with the expected measured value progressions a smaller deviation compared with the expected measured value progression for the process class CIP-process than compared with the expected measured value progression for the process class SIP-process. Correspondingly, the process B is identified as a CIP-process.

For determining the state of the measuring transducer 4, 5 such as described based on the preceding example, for each identified SIP- and each identified CIP-process, which the measuring transducer 4, 5 experiences, a corresponding loading value can be added as contribution to the total loading. As described, the total loading can be compared with a predetermined maximum loading value and in the case of reaching or shortly before reaching the maximum loading value an alarm can be output.

The deviation values found by the classifier in the identifying of the process currently being performed in the process container 2 for the currently registered, measured value progression compared with the expected measured value progression of the identified process can, in each case, be taken into consideration for determining the measuring transducer state. This will be described below in more detail.

THIRD EXAMPLE

In a third example of an embodiment, the process currently being performed in the process container 2 is identified by input of a user or by information from the control station 12 controlling the process. In this case, the state of the measuring transducer can be followed in manner as described in the above examples by adding corresponding loading values for each loading process, here CIP- or SIP-processes, to the total loading of the measuring transducer 4, 5.

An actual, current state of the measuring transducer can be determined in this example based on the deviation of the current actually registered measured value progression from the expected measured value progression of the process identified by means of the user input or the control station information. From this, a deviation value can be ascertained. If the deviation value deviates from a tolerance range defined by a predetermined quality criterion, the measuring transducer can output a warning- or alarm signal via the display or via the connection with the process control station 12.

To the extent that the deviation value lies still within the tolerable range predetermined by the quality criterion, the deviation value can be taken into consideration for determining the measuring transducer state in the same manner as the deviation values ascertained in the first and second examples, such as is described in the following.

FOURTH EXAMPLE

Evaluating the Registered Deviation Values

The deviation values ascertained in all of the above described Examples can be included into the determining of the measuring transducer state. As already described above, this has the advantage that the deviation values represent the actual state of the particular example of a measuring transducer.

On the one hand, the currently determined deviation value can be taken into consideration as such for state determination. For example, a threshold value for the deviation value can be predetermined, wherein in the case of exceeding the threshold value the measuring transducer is subjected to maintenance, respectively is replaced.

In such case, it is to be taken into consideration that a deviation from the expected measured value progression is not necessarily caused by a worsening of the measuring transducer state. Thus, a detected deviation from the expected measured value progression could result from not conducting the process currently being performed in the process container A, B in the correct manner. It is therefore advantageous to take measured values of a second measuring transducer into consideration, in order to differentiate whether a detected deviation from the expected behavior is caused by a change of the measuring transducer state or by a change of the process being performed in the process container. In the present example, are for this purpose, two same type pH measuring transducers 4, 5 with integrated temperature measuring sensor are integrated in the process container 2 for registering pH- and temperature measured values. It is also possible to provide two different measuring transducers 4, 5, for example, a pH measuring transducer and a conductivity sensor, in order to distinguish whether the detected deviation from the expected behavior of the one measuring transducer is to be attributed to a change of the measuring transducer or to a change in the process currently being performed in the process container.

Since as supplemental parameter one or more process parameters, e.g. pressure, temperature, pH-value, flow, the concentration of a substance in a medium present in the process container or one or more other supplemental parameters, e.g. sensor characteristics, such as a glass membrane resistance or a diaphragm resistance, can be ascertained and taken into consideration for the state determination, it can be distinguished whether an ascertained deviation of the currently registered, measured value progression from an expected progression is caused by a deviation of the measuring transducer behavior from an expected behavior or by a deviation of the process from an expected behavior. Fundamentally, three cases are thinkable for bringing about the deviation of the measured values delivered by the measuring transducer 4 from an expected measured value progression:

1. The measuring transducer has a defect or is at least maintenance needy to such a degree that reliability of its measured values is no longer assured (=measuring transducer malfunctioning), while the process runs within the desired limits (=process in order).
2. The measuring transducer is in a faultless state (=measuring transducer in order), while the process is not running within the desired limits (=process malfunctioning).
3. The measuring transducer has a defect or is at least maintenance needy to such a degree that reliability of its measured values is no longer assured (=measuring transducer malfunctioning) and the process is not running within the desired limits (=process malfunctioning).

In each of these cases, it is desirable that the measuring transducer or a superordinated unit connected with the measuring transducer output a warning or an alarm.

The classifier can be embodied to evaluate based on the measured value progression registered by the measuring transducer 4, with additional referencing of a measured value progression registered by the other measuring transducer 5, or one or more supplemental parameters. In this way, it is detectable whether the cause for a deviation of the measured value progression from the expected curve of the identified process is caused by the measuring transducer or by the process or by both.

For example, it can be decided based on a comparison of the classification of the current process based on the measured value progressions registered by both measuring transducers 4, 5 and the ascertained associated deviation values, which of the four cases, "measuring transducer and process in order", "process in order, measuring transducer malfunctioning", "measuring transducer in order, process malfunctioning" and "measuring transducer malfunctioning, process malfunctioning" is present.

Figure 4:
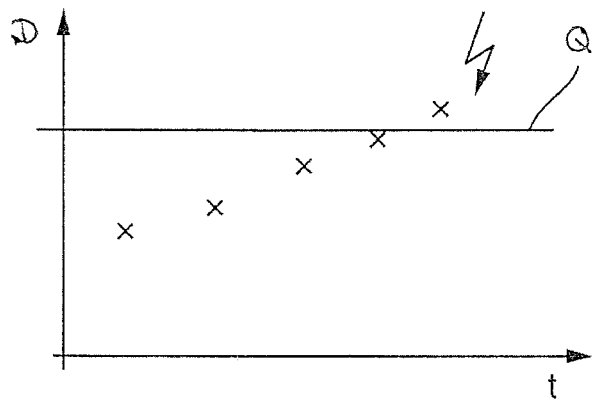
FIG. 4 is a first progression of the deviation values ascertained over a number of SIP-cycles.

FIG. 4 shows as a function of time a first progression of deviation values D ascertained over a number of SIP-processes cyclically performed in the process container 2. The deviation values continuously increase with increasing number of SIP-cycles, to which the measuring transducer 4 is exposed. The greater the deviation between the expected curve and the actually registered progression, the more strongly the measuring transducer 4 deviates from the ideal behavior. The deviation values can consequently be used as an indicator of the actual state of the measuring transducer. If a predetermined quality threshold value Q for the deviation value is exceeded, then the end of the life of the measuring transducer has been reached and it must be replaced.

Figure 5:
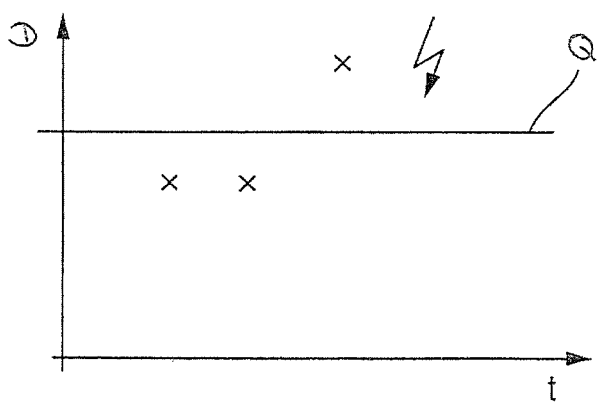
FIG. 5 is a second progression of the deviation values ascertained over a number of SIP-cycles.

FIG. 5 shows as a function of time a second progression of deviation values D ascertained over a number of SIP-processes cyclically performed in the process container 2. The measuring transducer example underpinning these values shows an abrupt worsening in the case of the third measured value, which possibly is attributable to a suddenly appearing defect of the measuring transducer. The measuring transducer must in this instance already be replaced after the third cycle.

By registering and evaluating a supplemental parameter by means of a second measuring transducer 5, it can be checked whether this abrupt change is attributable to a defect of the measuring transducer 4 or to a defect of the process being performed in the process container 2.

The measuring transducer state derived can be determined based on the deviation value and actions derived therefrom, such as, for example, replacing the measuring transducer, such as above described.

It is supplementally or alternatively possible to include the deviation values or variables derived therefrom into the above described total loading of the measuring transducer.

As above described, the here described method in each of the illustrated variants is applicable to a large number of different measuring transducers and a large number of different processes. Depending on the type of method, in such case, other measured variables than temperature and pH-value, especially pressure, conductivity, flow, turbidity (entrained dirt) of the process medium or other variables, can be taken into consideration.

The invention claimed is:

1. A method for determining a state of a measuring transducer integrated in a process container, comprising the steps of:
   identifying a process currently being performed in the process container, wherein one or more processes are being performed in the process container; and
   ascertaining a deviation value as measure of a deviation of a measured value progression registered by the measuring transducer during the process currently being performed in the process container from a measured value progression expected for the identified process, wherein the measuring transducer registers at least one physical or chemical process parameter within the process container,
   wherein the state of the measuring transducer and/or of the process is determined utilizing the deviation value, and
   wherein the process currently being performed in the process container is identified using a classifier such that the classifier associates the currently registered, measured value progression or at least one or more features of the measured value progression with a predetermined process class and determines as the deviation value a probability, with which the current measured value progression represents a process of the process class.

2. The method as claimed in claim 1, wherein:
   the process currently being performed in the process container is identified based on the measured value progression of the process parameter currently registered by means of the measuring transducer.

3. The method as claimed in claim 1, further comprising the step of:
   comparing the currently registered, measured value progression with at least one expected measured value progression, which represents a predetermined process class, wherein:
   in the case of sufficiently small deviation of the currently registered, measured value progression from the expected measured value progression, the process currently being performed in the process container and providing the basis for the currently registered, measured value progression is identified as a process of the predetermined process class.

4. The method as claimed in claim 3, further comprising the step of:

comparing the currently registered, measured value progression and the expected measured value progression based on one or more features of the measured value progressions, especially based on the measured value progression, a gradient of the measured value progression, an exceeding of a threshold value, a subceeding of a threshold value, a local or absolute extreme of the measured value progression, a noise superimposed on the measured value progression or a plateau of the measured value progression.

5. The method as claimed in claim 1, wherein:
the classifier is presented in a learning phase with one or more expected measured value progressions of the at least one process parameter, which measured value progressions represent the process class.

6. The method as claimed in claim 5, wherein:
the classifier extracts by means of a machine learning method features of the one or more expected measured value progressions and associates the features with the process class.

7. The method as claimed in claim 1, wherein:
the one or more expected measured value progressions are predetermined based on pretrials using a measuring transducer different from the measuring transducer but comparable as regards accuracy of measurement, dynamic range and measuring range, integrated at the location of use of the measuring transducer in the process container.

8. The method as claimed in claim 1, wherein:
the process currently being performed in the process container is identified based on information from a process control controlling the process currently being performed in the process container.

9. The method as claimed in claim 1, wherein:
the process currently being performed in the process container is identified based on information input by a user of a measuring and evaluation circuit of the measuring transducer.

10. The method as claimed in claim 1, wherein:
the one or more processes are performed repeatedly during the lifetime of the measuring transducer in the process container, a change of the respectively ascertained deviation values is determined, and the state of the measuring transducer is determined based on the change.

11. The method as claimed in claim 10, wherein:
a time development of the repeatedly ascertained deviation values is used for determining the state of the measuring transducer, especially for predicting a remaining life of the measuring transducer.

12. The method as claimed in claim 1, wherein:
by means of a predetermined quality criterion, the currently ascertained deviation value is classified either as tolerable or as not tolerable; and
in the case, in which the deviation value is classified as not tolerable, an alarm or a warning is triggered.

13. The method as claimed in claim 1, wherein:
by means of the measuring transducer itself or by means of an additional, auxiliary, measuring transducer likewise integrated in the process container, at least one supplemental parameter is registered, which enters into determining the state of the measuring transducer and, in given cases, into an additional determining of a state of the process currently being performed in the process container.

14. The method as claimed in claim 1, wherein:
the measuring transducer registers measured value progressions of at least two different process parameters, the process currently being performed in the process container is identified, for example, based on the currently registered, measured value progressions; and
relative to a process parameter, preferably relative to all process parameters, in each case, a deviation value as measure of a deviation of a measured value progression registered by the measuring transducer during the process currently being performed in the process container from a measured value progression expected for the identified process is ascertained.

15. The method as claimed in claim 1, wherein:
the ascertaining of the deviation value and the determining of the state of the measuring transducer based on the ascertained deviation value is performed by an evaluation circuit, which is at least partially a component of the measuring transducer and/or at least partially a component of a superordinated data processing unit connected with the measuring transducer, especially a measurement transmitter, a computer or a programmable logic controller.

16. An apparatus for performing a method for determining a state of a measuring transducer integrated in a process container, wherein in the process container one or more processes are being performed, and a measuring transducer registers at least one physical or chemical process parameter within the process container, the method comprising the steps of identifying a process currently being performed in the process container, and ascertaining a deviation value as measure of a deviation of a measured value progression registered by the measuring transducer during the process currently being performed in the process container from a measured value progression expected for the identified process, wherein the state of the measuring transducer and/or of the process is determined utilizing the deviation value, and wherein the process currently being performed in the process container is identified using a classifier such that the classifier associates the currently registered, measured value progression or at least one or more features of the measured value progression with a predetermined process class and determines as the deviation value a probability, with which the current measured value progression represents a process of the process class, and the apparatus comprising:
a process container;
at least one measuring transducer integrated therein; and
a data processing system comprising at least one processor and a program memory for performing a program furnished in the program memory for identifying a process currently being performed in the process container, for ascertaining a deviation value as measure of a deviation of a measured value progression registered by the measuring transducer during the process currently being performed in the process container from a measured value progression expected for the identified process, and for ascertaining the state of the measuring transducer based on the deviation value.

* * * * *